United States Patent [19]

Gold

[11] 4,156,426

[45] May 29, 1979

[54] HEAD-MOUNTED OXYGEN-ADMINISTRATION DEVICE

[76] Inventor: Lawrence W. Gold, 1286 Larch Ave., Moraga, Calif. 94556

[21] Appl. No.: 823,657

[22] Filed: Aug. 11, 1977

[51] Int. Cl.² .......................................... A61M 15/00
[52] U.S. Cl. .................................. 128/205; 128/206; 128/208; 128/203
[58] Field of Search .................... 128/206, 140 N, 205, 128/207, 208, 195, 196, 197, 198, 199, 200, 201, 342, 173 R, 348

[56] References Cited

U.S. PATENT DOCUMENTS

| | | | |
|---|---|---|---|
| 853,431 | 5/1907 | Allen | 128/207 |
| 2,546,214 | 3/1951 | Curry | 128/173 R |
| 2,763,263 | 9/1956 | Ellman | 128/198 |
| 3,902,486 | 9/1975 | Guichard | 128/140 N |

FOREIGN PATENT DOCUMENTS 156627 2/1904 Fed. Rep. of Germany ........... 128/205

*Primary Examiner*—Henry J. Recla
*Attorney, Agent, or Firm*—Warren, Chickering & Grunewald

[57] ABSTRACT

A head-mounted oxygen-administration device designed to improve the level of inspired oxygen concentration for mouth and nasal breathing users without interference with the user's activities of eating and talking and which includes a pair of nasal cannulas mounted on one side of a body having a chamber adapted for connection to a source of oxygen under pressure providing a positive oxygen flow into the chamber, and a flow discharge aperture provided on the opposite side of the body in communication with the chamber and functioning upon restriction of nasal inhalation and during oral inhalation to direct oxygen flow from the chamber to the user's mouth, such directed flow being effected from a position remote from the user's mouth.

7 Claims, 6 Drawing Figures

HEAD-MOUNTED OXYGEN-ADMINISTRATION DEVICE

BACKGROUND OF THE INVENTION

1. Field of Invention

The invention relates to oxygen-administration devices of the nasal cannular type such as disclosed in U.S. Pat. Nos. 2,868,199; 3,513,844; and 3,802,431.

2. Description of Prior Art

Good oxygenation is assured by the administration of oxygen by the conventional face mask. However, face masks are frequently intolerable to patients and, of course, cannot be used during the time a person is fed or is eating. Nasal cannulas of the type illustrated in the above-noted patents generally provide less adequate oxygenation, but are more readily tolerable in most instances by patients. This lesser degree of oxygenation is compromised even further in the instance of patients who breathe through their mouths.

SUMMARY OF THE INVENTION

The device of the present invention provides the comfort and convenience typical of the standard nasal cannula while at the same time providing a higher level of inspired oxygen concentration regardless of the relative proportions of mouth and nasal breathing.

An object of the present invention is therefore the provision of a head-mounted oxygen-administration device which may be used with comfort and convenience by the patient and which will insure more successful oxygenation than devices currently in use.

The invention possesses other objects and features of advantage, some of which of the foregoing will be set forth in the following description of the preferred form of the invention which is illustrated in the drawings accompanying and forming part of this specification. It is to be understood, however, that variations in the showing made by the said drawings and description may be adopted within the scope of the invention as set forth in the claims.

DETAILED DESCRIPTION OF THE INVENTION

Figure 1:
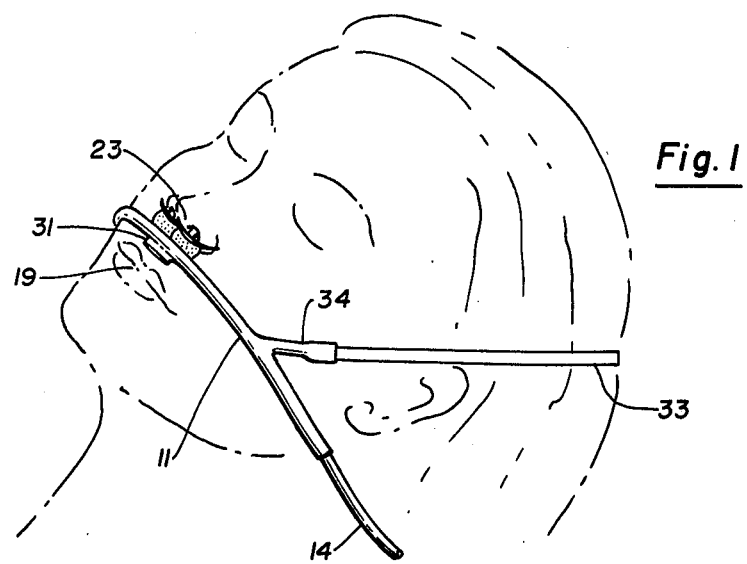
FIG. 1 is a perspective view of an oxygen-administration device constructed in accordance with the present invention.

The head-mounted oxygen-administration device of the present invention comprises, briefly, tubular passage means 11 providing a chamber 12 having an inlet 13 adapted for connection to an oxygen source (not shown) via conduit 14; nasal cannualas 16 and 17 mounted on means 11 at one side thereof and formed for insertion into the nares of the user; and a flow-discharge aperture 18 provided on the opposite side of means 11 in communication with chamber 12 for directing oxygen in the direction of the user's mouth 19.

Figure 2:
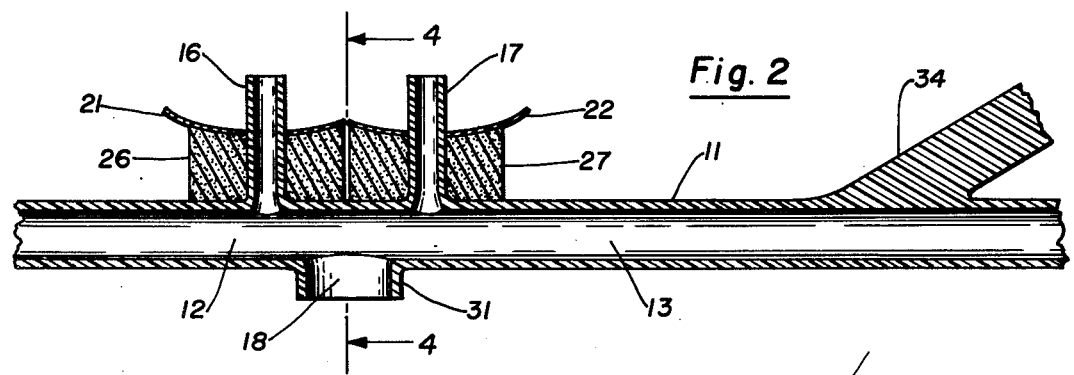
FIG. 2 is a fragmentary cross-sectional view of the device on an enlarged scale.
Figure 3:
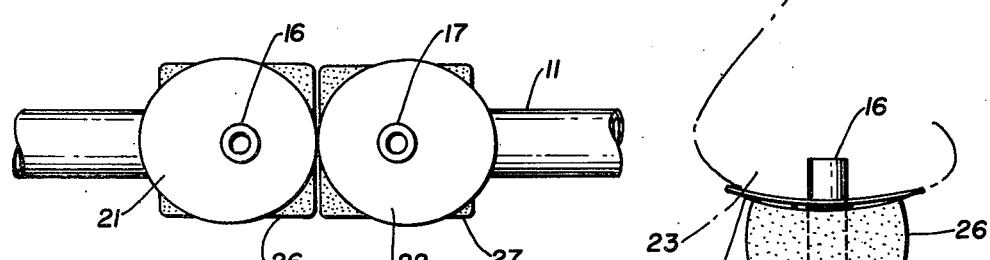
FIG. 3 is a top plan view of the device.
Figure 4:
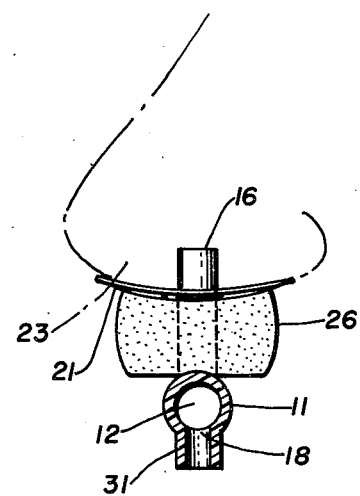
FIG. 4 is a cross-sectional view of the device taken substantially on the plane of line 4—4 of FIG. 2.

In the embodiment of the invention shown in FIGS. 1-4, flap valves 21 and 22 are mounted on cannulas 16 and 17 in position for and movable into and from engagement with the inferior nasal surface 23 for sealing the cannulas 16 and 17 into the nares of the user upon nasal inhalation and for passing spent air from the nares on nasal expiration. As here shown, these valves comprise flexible sheets of disc shape which are secured and sealed to the cannulas and extend radially therefrom, as seen in FIG. 3. As will be understood, the flexible sheets 21 and 22 will move upwardly into engagement with the inferior nasal surface 23 upon nasal inhalation of the user so as to preclude or at least minimize the entry of atmospheric air into the nares during inhalation. At the same time, flap valves 21 and 22 are free to move in the opposite direction away from the inferior nasal surface during expiration so as to freely pass air along a parallel route between the exterior of the cannulas and the interior of the nares.

Another feature of the present construction is the use of means 26 and 27 for biasing sheets 21 and 22 upwardly toward the inferior nasal surface and which also assist in the contour fitting of the flexible sheets to the nasal surface. As here shown, means 26 and 27 comprise a pair of deformable, resiliently self-restoring members which are mounted in surrounding relation to the cannulas in engagement with the confronting surfaces of members 21-22 and 11 and for compression therebetween. These members may be formed of soft plastic foam pads so as to provide a soft, comfortable compression of members 21 and 22 against the underside of the nose around the nostrils in good conformity thereto, providing an effective seal on nasal inhalation. At the same time, the soft, yielding pads will readily compress further in response to the opposite expiration pressure to release the spent air, thus providing significantly greater inspired oxygen concentration with complete comfort to the patient.

As hereinabove noted, one of the principal disadvantages of the conventional nasal cannular device is its failure to provide oxygenation when a patient shifts to partial or full mouth breathing. The present structure automatically accommodates for this change of breathing in the automatic discharge of oxygen through aperture 18 when the patient shifts to mouth breathing; and as above observed, the oxygen escaping through aperture 18 is directed into the proximity of the user's mouth so that an effective level of inspired oxygen concentration is maintained. To assist in this function, aperture 18 and the discharge therefrom are embodied in a duct 31 which is connected to the tubular manifold 11 and extends downwardly therefrom to lead the escaping oxygen into the proximity of the user's mouth. Preferably, the length of duct 31 is such as to extend approximately midway between the inferior nasal surface 23 and the mouth 19 so as to not interfere with the functioning of the mouth in eating, talking, etc.

As will be observed from FIG. 2, cannulas 16 and 17 will have a normal lateral spacing for insertion in the nares and the longitudinal flow axis of duct 18 is generally medially between the flow axes of the cannulas. The usual nasal cannular head-mounted structure is here used comprising an elastic strap 33 secured to a tie portion 34 formed on tubular member 11 adjacent conduit 14 and extending around the head of the user to the opposite closed end (not shown) of member 11.

Figure 5:
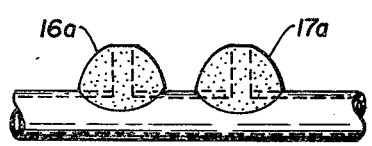
FIG. 5 is a fragmentary side elevation of a modified form of the device.
Figure 6:
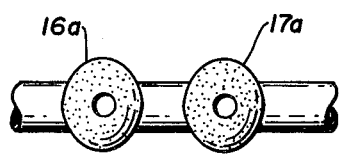
FIG. 6 is a top plan view of the device illustrated in FIG. 5.

A modified form of the invention is illustrated in FIGS. 5 and 6, wherein the cannulas 16a and 17a are formed as tapered mounds for snug fitting within the nares, thus providing the desired seal upon nasal inhalation without the use of flap valves 21 and 22. On nasal exhalation, spent air may flow freely through the interior passages in the cannulas and out through port 18. Mounds 16a and 17a may be formed of soft compressible material, such as foam plastic, and may be elongated into an oval shape, as seen in FIG. 6, for better conformity to the oval shape of the nasal passages.

In the use of the device the oxygen flow rate may be adjusted to provide desired inspired oxygen concentrations which, as above noted, may be significantly greater than those achieved by current nasal cannular devices. If resting ventilation does not exceed oxygen flow rate, a high concentration of oxygen will be inspired. Should ventilation exceed oxygen flow rate, the inferior aperture 18 will admit room air which will be mixed with oxygen; and should nasal breathing not occur, aperture 18 will redirect oxygen to the proximity of the mouth, where oxygenation will continue.

What is claimed is:

1. A head-mounted oxygen-administration device comprising:
    passage means providing a chamber having a longitudinal dimension adapted to extend at least under the nose of a user and having an inlet adapted for connection to a source of oxygen under pressure providing a positive oxygen flow into said chamber;
    nasal cannula means mounted on said passage means at one side thereof and extending perpendicularly to said longitudinal dimension of said chamber and being in communication with said chamber and formed for insertion into the nares of the user and providing nasal oxygen induction upon nasal inhalation;
    means flow discharge aperture provided on said means directly opposite said nasal cannula means thereby being remote from the user's mouth and being in communication with said chamber and functioning upon restriction of nasal inhalation and during oral inhalation to direct oxygen flow from said chamber to the user's mouth head mounting means for securing said passage means to the head of a user whereby said nasal cannula means are positioned in each respective nostril.

2. The device of claim 1, and a duct providing said aperture means and connected to said passage means and extending therefrom for leading oxygen from said chamber into the proximity of the user's mouth.

3. The device of claim 2, said cannula means being spaced apart along substantially parallel flow axes, and the flow axis of said duct being medially between the flow axes of said cannula means.

4. The device of claim 1, and flap valves mounted on said cannula means in position for and movable into and from engagement with the inferior nasal surface for sealing said cannula means in said nares upon nasal inhalation and passing spent air from said nares on nasal expiration.

5. The device of claim 4, said valves each comprising a flexible sheet secured and sealed to each cannula means and extending radially therefrom; and
    means biasing each sheet toward said inferior nasal surface comprising a deformable, resiliently self-restoring member surrounding each cannula means in engagement with and for compression between each sheet and said passage means.

6. The device of claim 1, and means on said cannula means providing a substantially sealed engagement with said nares comprising a pair of upwardly tapered mounds of soft compressible material engageable with said nares.

7. A method for improving the level of inspired oxygen concentration for mouth and nasal breathing users without interference with the user's activities of eating and talking comprising:
    inserting into the nares of a user nasal cannulas mounted perpendicularly to one side of a chamber having a longitudinal dimension adapted to extend at least under the nose of a user and having an inlet adapted for connection to a source of oxygen under pressure providing a positive oxygen flow into said chamber, said chamber having a discharge aperture directly opposite said nasal cannulas;
    directing a flow of oxygen under pressure into said cannulas during the user's nasal inhalation; and
    directing away from said cannulas through said aperture said oxygen flow into the region of the user's mouth during periods of oral inhalation.

* * * * *

UNITED STATES PATENT AND TRADEMARK OFFICE
CERTIFICATE OF CORRECTION

PATENT NO. : 4,156,426
DATED : May 29, 1979
INVENTOR(S) : LAWRENCE W. GOLD

It is certified that error appears in the above-identified patent and that said Letters Patent are hereby corrected as shown below:

In the Claims:

Column 3, line 39, delete "means" and after "aperture" insert ---means---; and line 46, after "mouth" insert ---;--- and start a new paragraph with the word "head".

Signed and Sealed this

Twenty-eighth Day of August 1979

[SEAL]

Attest:

LUTRELLE F. PARKER

Attesting Officer     Acting Commissioner of Patents and Trademarks